United States Patent [19]

Sato et al.

[11] Patent Number: 4,716,108
[45] Date of Patent: Dec. 29, 1987

[54] ASSAYING ANTI-TP IGM ANTIBODIES FOR SYPHILIS DIAGNOSIS

[75] Inventors: Takashi Sato, Saitama; Emiko Kubo; Takako Kayashima, both of Tokyo, all of Japan

[73] Assignee: Fujirebio Kabushiki Kaisha, Tokyo, Japan

[21] Appl. No.: 833,666

[22] Filed: Feb. 24, 1986

Related U.S. Application Data

[63] Continuation of Ser. No. 513,411, Jul. 14, 1983, abandoned.

[30] Foreign Application Priority Data

Jul. 14, 1982 [JP] Japan ................. 57-121244

[51] Int. Cl.$^4$ ............... G01N 33/53; G01N 33/555; G01N 33/569; G01N 33/571
[52] U.S. Cl. ...................... 435/7; 436/511; 436/513; 436/520; 436/523
[58] Field of Search .............. 435/7; 436/511, 513, 436/520, 523

[56] References Cited

U.S. PATENT DOCUMENTS

| | | | |
|---|---|---|---|
| 4,184,849 | 1/1980 | Cambiaso | 436/523 |
| 4,308,026 | 12/1981 | Mochida | 436/520 |
| 4,313,927 | 2/1982 | Fridlender . | |
| 4,403,037 | 9/1983 | Coates | 436/520 X |

FOREIGN PATENT DOCUMENTS

| | | |
|---|---|---|
| 38181 | 10/1981 | European Pat. Off. . |
| 38150 | 10/1981 | European Pat. Off. . |
| 1563355 | 3/1980 | United Kingdom . |
| 2045431 | 10/1980 | United Kingdom . |

OTHER PUBLICATIONS

Chemical Abstracts I, 96:33217z (1982).
Chemical Abstracts II, 97:37437b (1982).
Chemical Abstracts III, 97:123443g (1982).
Chemical Abstracts IV, 99:86518d (1983).
Chemical Abstracts V, 100:155090m (1984).

*Primary Examiner*—Sidney Marantz
*Attorney, Agent, or Firm*—Burgess, Ryan and Wayne

[57] ABSTRACT

A method of measuring an infectious disease antibody such as syphilis IgM, which comprises treating immunoglobulins of a sample with an anti immunoglobulin antibody sensitized on carrier particles and an antigen of the infectious disease sensitized on carrier particles. According to the method of the invention, the specific antibody of the specific infectious disease such as syphilis IgM can easily and exactly be measured. This method is useful for the judging the stage of infectious disease and watching the results of treatment.

4 Claims, No Drawings

ASSAYING ANTI-TP IGM ANTIBODIES FOR SYPHILIS DIAGNOSIS

This application is a continuation of U.S. Ser. No. 513,411, filed July 14, 1983, now abandoned.

This invention relates to a method of measuring an infectious disease antibody such as a syphilis antibody, and more particularly, this invention relates to a method of measuring the individual immunoglobulins such as IgM, IgG and IgA, of a particular infectious disease.

For instance, with regard to diagnosing methods of syphilis, there are the STS (Serologic Test for Syphilis) method of using cardiolipin which is a lipoidal antigen and the method of using Treponema pallidum (hereinafter referred to as TP) as an antigen.

The STS method including the VDRL method, the RPR (Rapid Plasma Reagin Card Test) method, the agglutination method, Ogata's method, and Kolmer's method, occasionally produce a biological false positive result due to the antigen which is not TP.

As regards the method of using TP antigen, the TPI (Treponema Pallidum Immobilization) method, FTA-Abs (Fluorescent Treponemal Antibody Absorption) method, and the TPHA (Treponema Pallidum Hemagglutination) method are known. Among them, the TPHA method developed the automatic operation of the micro titer method, and now is widely employed as a typical method of diagnosing syphilis.

The erroneous indication of the biological false positive of this TP antigen using a method such as the TPHA method, is less than that of the STS method. However, this method is not always suitable for watching the progress of syphilis after treatment and for judging the cure because it catches all TP antibodies (for example, Yoshio Fukuoka, Nippon Rinsho, vol. 38, p 1501 (1980)). Thus, the conventional method using TP antigen cannot distinguish the IgM produced at the primary stage of syphilis, the IgG produced at its latter stage and other immunoglobulins.

In 1979, B. Schmidt reported that judgments of the stage of syphilis and the necessity of treatment can be made by measuring the syphilis IgM according to the SPHA (Solid Phase Hemadsorption) method using anti human IgM antibody and erythrocytes sensitized with TP (Bruno Schmidt), Sex. Trans. Dis., vol. 7, pp 53–58 (1980)). This procedure is simpler than that of the prior method of IgM-FTA-Abs (P. O'Neil, Br. J. Vener. Dis., vol 48, pp 460–463 (1972). However, the sensitivity against primary syphilis using this method is low and the rate of false negative of this method is high.

On the other hand, F. Muller et al. separated the IgM fraction and IgC fraction from serum by a gel filtration method and as to each fraction, they achieved 19S (IgM)-TPHA and 19S (IgM)-FTA-Abs. They judged the stage of syphilis by the results and used it in judging the degree of curing (F. Muller, WHO/-VDT/RES., vol. 79, p 361 (1979)). However, this gel filtration method requires a particular apparatus, an involved procedure, and also consumes a substantial amount of TPHA reagents. Furthermore, it does not detect a lower molecule of (8S) IgM which is often found in the case of autoimmune disease since IgM and IgG are separated from each other according to the difference of their molecular sizes in this method (F. Muller, Klinische Wochenschrift, vol. 57, pp 667–671 (1979)).

It has now been found that when immunoglobulins of a sample are treated with an anti immunoglobulin antibody sensitized on carrier particles and an antigen of an infectious disease sensitized on carrier particles, the specific antibody such as IgM, IgG and IgA against the specific infectious disease can be measured. According to the method of the invention, immunoglobulins of a sample are contacted with an anti immunoglobulin antibody which is able to react with the above infectious disease antibody to be measured and which is sensitized on carrier particles or an antigen which is derived from an infectious disease and which is sensitized on carrier particles in a solution to react with one or more kinds of the above immunoglobulins and the carrier particles are separated from the solution. Then, the immunoglobulin(s) is recovered by the above reaction, separated and contacted with the remaining carrier particles of the above two kinds of carrier particles, and accordingly, the specific antibody of the aforementioned infectious disease can be measured.

The immunoglobulins are antibodies of an infectious disease and include IgM, IgG, IgA, IgE and IgD. The infectious disease are not limited to syphilis and includes various viral diseases such as rubella, herpes, mumps, ATLV (Adult T-cell leukemia virus) infection, and cytomegalo infection, and other infectious diseases such as, for example, toxoplasmosis. The sample containing such immunoglobulins is usually the serum of a person to be diagnosed as the infectious disease or its diluted solution. This sample is pretreated by pH adjustment, by centrifuging or by the addition of a stabilizer, if necessary.

The anti immunoglobulin antibody is the anti IgM antibody and anti IgG antibody. This anti antibody is able to react with the infectious disease antibody to be measured.

The anti antibody may be prepared according to the conventional manner. Specifically, the particular kind of the immunoglobulin which usually originates in humans is injected into a warm-blooded animal such as a rabbit, sheep, guinea pig or a chicken, and the anti antibody appearing in its blood is collected. The anti antibody may alternatively be produced as a monoclonal antibody. In this case, the particular kind of the immunoglobulin is injected into, for example, the abdominal cavity of a BALB/C strain mouse, and its spleen is isolated after two weeks. The spleen cell is fused with a mouse myeloma P3U1 cell by a conventional method such as by using polyethylene glycol. The hybridoma thus obtained is cultured and cloned. The cell capable of producing the anti antibody so produced is injected into the abdominal cavity of a mouse, and multiplied. Then, ascites are collected and the anti antibody is separated from the ascites.

The anti antibody is separated from blood, ascites, etc. and purified by the conventional method of separating immunoglobulin such as by precipitation using ammonium sulfate, ion-exchange chromatography using DEAE-cellulose, the gel filtration method, or affinity chromatography.

The anti antibody is not limited to the native anti antibody, and includes the digestion product by pepsin such as an F(ab')2 fragment.

Such an anti antibody is sensitized on carrier particles. The carrier particles may be the usual ones for the passive hemagglutination (PHA) method and include various erythrocytes and chicken erythrocytes such as sheep erythrocytes and chicken erythrocytes, microbial cells, polystyrene latex, and gelatin particles (U.S. Pat. No. 4,416,813 and European Patent Application Ser.

No. 82301235.6). The sensitization method of the anti antibody on the carrier particles may also be a conventional one and includes the method of using tannic acid, the method of using formalin, the method of using glutaraldehyde, the method of using bisdiazotized benzidine, the method of using pyruvic aldehyde and the method of using toluene-2,4-diisocyanate.

The contacting of the immunoglobulins with the anti immunoglobulin antibody sensitized on carrier particles may be carried out according to the conventional procedures of the reverse passive hemagglutination (RPHA) method. In this case, the sample solution containing the immunoglobulins is first diluted with a diluent and the dilution series of the sample solution such as twice by twice dilution series and four times by four times dilution series, is prepared. To the above diluent may preferably be added an absorbing agent for the elimation of non-specific reactions. The suspension of the anti immunoglobulin antibody sensitized on carrier particles is prepared and added to the dilution series of the sample solution. The mixture is incubated at 20° to 40° C. for an instant up to 120 minutes. Other than the above, the sample solution may be contacted with the anti immunoglobulin antibody sensitized on carrier particles and the immunoglobulin reacted with the anti immunoglobulin antibody sensitized on carrier particles is divided to prepare the dilution series after the recovery of the carrier particles described below. In this case, the immunoglobulin may be released from the carrier particles prior to the preparation of the dilution series.

After the incubation, the carrier particles are separated from the solution and the unreacted immunoglobulins are thereby removed. The separation may be carried out by centrifuging or filtering. The recovered carrier particles may preferably be washed several times by suspending in water, a saline solution or a buffer solution containing some absorbents by means of vibration, stirring or treating with ultrasonics and recovering by centrifuging or filtering.

The washed carrier particles are suspended in a solution such as a diluent of the PHA method to form the dilution series of the recovered immunoglobulin. In the case where the immunoglobulin is released from the carrier particles, the dilution series is usually constituted of solutions alone.

The antigen to be added to the dilution series is derived from the infectious disease of which the antibody is measured. Thus, when the infectious disease is syphilis, the antigen is obtained from a culture of TP such as destroyed cells of TP. The carrier particles on which the antigen is sensitized may be the usual ones for the PHA method and the sensitization may also be a conventional method. Thus, for instance, when the infectious disease is syphilis, the commercial product of TP sensitized carrier particles may be employed as the antigen in the method of the present invention.

Such an antigen sensitized on carrier particles is contacted with the dilution series of the recovered immunoglobulin. The contacting may be carried out according to the conventional procedure of the PHA method. Thus, the antigen sensitized on carrier particles is suspended in a reconstituting solution and added to the dilution series of the recovered immunoglobulin. Then, the mixture is incubated at 4° to 40° C. usually at room temperature, for 30 minutes to 25 hours and the pattern of the carrier particles of each well is observed as to whether agglutination occurs or not.

In the method of the invention, one immunoglobulin is selected according to its class such as IgM or IgG, through the contacting with the anti immunoglobulin antibody sensitized on carrier particles, and the specific immunoglobulin is selected according to its origin such as TP antigen and the antigen of other infectious diseases by contacting with the antigen sensitized on carrier particles.

Accordingly, the immunoglobulins of a sample need not be contacted first with the anti immunoglobulin antibody. Instead, they may first be contacted with the antigen sensitized on carrier particles in a solution to react with the immunoglobulins of the particular infectious disease, the carrier particles are separated from the solution and the immunoglobulins recovered by the above reaction and separation are then contacted with the anti immunoglobulin antibody sensitized on carrier particles. In this case, the separated carrier particles must be washed sufficiently or else the false positive ring of hemagglutination appears.

The reagents necessary for the method of the invention are absorbing solutions and a diluent other than the antigen sensitized on carrier particles and the anti immunoglobulin antibody sensitized on carrier particles. As to the absorbing solutions, two kinds are necessary. One is for the antigen sensitized on carrier particles, and the other is for the anti immunoglobulin antibody sensitized on carrier particles. On the other hand, the diluent may be combined with the absorbing solution to make the mixture. Other than the above, a standard serum, unsensitized carrier particles and a reconstituting solution are usually employed. These reagents may be the same as those employed in the PHA method and the RPHA method.

The method of the invention is superior in specificity. According to the instant method, a specific antibody of a specifically infectious disease such as syphilis IgM is simply and rapidly measured by using conventional equipment. The data obtained by the method of the invention are useful for judging the stage of the infectious disease, watching of the results of treatment and judging the necessity of further treatment.

The present invention is further illustrated by the following examples.

EXAMPLE 1

(i) Preparation of TP Antigen

The strain of WHO pathogenic standard Treponema pallidum Nichols, obtained from the National Institute of Health, Ministry of Health & Welfare (Japan) was cultured and the multiplied cells were suspended at a concentration of $6.0 \times 10^7$ cells/ml.

One ml of the suspension was inoculated in the testes of each of 10 rabbits and cultured for 12 days. The testes were excised from each rabbit and minced. Multiplied cells were extracted from the minced testes by using 1000 ml of the mixed solution consisting of an equal volume of inactivated normal serum of rabbit and 1/7M saline solution.

The extracts were centrifuged at $200 \times g$ for 10 minutes and the precipitates were removed. The supernatant was centrifuged again at $19,000 \times g$ for 90 minutes, thereby precipitating the TP cells.

The precipitates containing the TP cells were washed three times with chilled 0.075M sodium oxalate and suspended in 10 ml of 1/15M phosphate buffer solution having a pH of 6.4. The number of TP cells in the suspension was counted and then the suspension was diluted so that the concentration of the TP cells was $2 \times 10^9$ ml to obtain a TP antigen solution.

13 ml of 17 w/v% of a sodium diatrizoate solution was placed in a 14 ml cellulose tube for ultracentrifugation and one ml of the TP antigen solution was layered on it. The cellulose tube was placed in a horizontal rotor SW4OTi of a centrifuge for separation (Beckman L8), and centrifuged at 4° C. at 23,500 rpm (100,000×g) for 45 minutes. The pelleted matter of TP cells at the bottom was collected and suspended in 8 ml. of a phosphate buffered saline solution (PBS) at a pH of 7.2. The TP cells were destroyed by a homogenizer (Tomy Seiko UR-200P, Tokyo, Japan), and and preserved at −80° C.

(ii) Preparation of TP Antigen Sensitized Erythrocytes 20 ml of a 2.5 v/v% formalinized sheep erythrocytes suspension suspended in PBS (pH 7.2) was mixed with 20 ml of a 10 ppm tannic acid PBS (pH 7.2) solution and incubated at 37° C. for 10 minutes. The erythrocytes were collected by centrifugation and washed with a saline solution. The washed erythrocytes were suspended in 20 ml of a PBS solution (pH 6.4).

The TP antigen solution was diluted 80 times, and 20 ml of the diluted TP antigen solution was mixed with 20 ml of the above washed erythrocytes suspension. The mixture was incubated at 37° C. for 40 minutes with stirring at intervals at 10 minutes.

The erythrocytes were collected by centrifuging and washed with saline solution containing 1% normal rabbit serum. The erythrocytes were suspended in 10 ml of a PBS solution (pH 7.2) containing 1% normal rabbit serum and each 0.5 ml of the suspension was pipetted into each 5 ml vial. Then, the erythrocytes in each vial were lyophilized and preserved at 4° C.

(iii) Preparation of Anti Human Immunoglobulin Antibody Sensitized Erythrocytes

Sheep erythrocytes were treated with tannic acid in the same manner as in the case of paragraph (ii) supra.

20 ml of the suspension of the sheep erythrocytes treated with tannic acid suspended in PBS (pH 6.4) was mixed with 20 ml of rabbit immunoglobulins to human IgM antibody-μ-chain specific, Dako) diluted 400 times and the mixture was treated in the same manner as set forth in the procedure of paragraph (ii) supra to produce a lyophilized product of the anti human IgM antibody sensitized erythrocytes.

Rabbit immunoglobulins to human IgA antibody α-chain specific Dako) and rabbit immunoglobulins to human IgG antibody (α-chain specific Dako) were also sensitized on sheep erythrocytes in the same manner as above and their lyophilized products were obtained.

(iv) Hemagglutination Immunoassay (HIA)

One ml. of distilled water was added to each of the above lyophilized products which were human IgM antibody sensitized erythrocytes (AM-RBC), anti human IgA antibody sensitized erythrocytes (AA-RBC), anti human IgG antibody sensitized erythrocytes (AG-RBC) and TP antigen sensitized erythrocytes (TP-RBC) and they were accordingly reconstituted.

5 μl of a sample serum was placed in a left end well (well No. 1) of a micro titer plate and 50 μl of B-solution (a combined solution of an absorbing solution with a diluent which is one of the components of the kit for TPHA test, manufactured by Fujizoki Pharmaceutical Co., Ltd.) was added to the same well. Each 25 μl of the B-solution was placed in each well from the second well (well No. 2) from the left end to the well of right end. Then the sample serum in the well No. 1 was diluted and a twice by twice dilution series of the sample serum was prepared.

The reconstituted AM-RBC suspension was diluted with 7 ml of the B-solution (corresponding to 8 times diluted suspension of 2.5% AM-RBC suspension) and each 25 μl of the diluted suspension was added to each well from the third well (well No. 3) from the left end to the right end well. 25 μl of unsensitized blood cells (RBC) suspension was added to the well No. 2.

The mixture in each well was sufficiently mixed by vibrating the micro titer plate and the plate was covered by a glass plate. The mixture was then incubated at 37° C. for 15 minutes and centrifuged at room temperature at 2,000 rpm (600×g) for 5 minutes. The supernatant of each well was aspirated and 25 μl of saline solution was added to each well. The blood cells in each well were suspended by vibrating the micro titer plate and centrifuged at 2000 rpm (600×g) for 5 minutes. Then, the supernatant of each well was aspirated again.

Each 25 μl of the B-solution was added to each well and the erythrocytes were suspended by vibrating. 25 μl of the reconstituted TP-RBC suspension was added to each well from the well No. 3 to the right end well. 25 ml of the RBC suspension was added to well No. 2. The mixture of each well was sufficiently stirred and allowed to stand for 2 hours or overnight. Then, the pattern of the erythrocytes of each well was read to determine whether hemagglutination occurred or not.

Antibody titer is expressed in the dilution ratio of serum and the case of an antibody titer greater than 40 is indicated as positive.

The procedure of the dilution is shown in the following table.

| Well No. | 1 | 2 | 3 | 4 | 5 | 6 | ... |
|---|---|---|---|---|---|---|---|
| Dilution Ratio of Serum | 10 | 20 | 40 | 80 | 160 | 320 | ... |
| Serum | 5 | 25 | 25 | 25 | 25 | 25 | ... |
| B-Solution | 50 | 25 | 25 | 25 | 25 | 25 | ... |
| AM—RBC | — | — | 25 | 25 | 25 | 25 | ... |
| RBC | — | 25 | — | — | — | — | — |
| B-Solution | — | 25 | 25 | 25 | 25 | 25 | ... |
| TP—RBC | — | — | 25 | 25 | 25 | 25 | ... |
| RBC | — | 25 | — | — | — | — | — |

As regards the cases of using AA-RBC and AG-RBC, the measuring procedures were the same as the above case of AM-RBC.

(v) Practical measurements

As to 3 sample sera of patients with primary syphilis, 3 sample sera of patients with secondary syphilis, 3 sample sera of patients with late latent syphilis and 5 sample sera of healthy persons, (the method of the above paragraph (iv) (HIA), the TPHA method (manufactured by Fujizoki Pharmaceutical Co., Ltd.), the FTA-Abs method (Pub. Health Rep., vol. 79, pp 410–412 (1964)), the RPR method (Pub. Health Rep., vol. 77 pp 645–652 (1962)), the Ogata method (Nisshin Igaku, vol. 47, pp 671–689 (1960)) and the gel filtration-TPHA method (Nippon Iji Shinpo, No. 3002, pp 43–47 (1981) were carried out.

The results are shown in the following table.

| Stage | Serum | HIA IgM | HIA IgA | HIA IgG | TPHA Old | TPHA New | FTA—Abs $\mu$ | FTA—Abs $\mu + \gamma$ | RPR | Ogata | Gel Filtration —TPHA 19S(IgM) —TPHA | Gel Filtration —TPHA 7S(IgG) —TPHA |
|---|---|---|---|---|---|---|---|---|---|---|---|---|
| Primary | H.A 8/12 | 160 | 80 | (—) | 20$^W$ | 320 | 20 | 20 | 1 | 10 | 2.1 | 0 |
|  | T.A 2/16 | 640 | 1280$^W$ | (—) | 80 | 640 | 20 | 80 | 16 | 160 | 10.2 | 0 |
|  | T.K 1/8 | 320 | 320 | (—) | 40 | 640 | 20 | 20 | 16 | 320 | 5.1 | 0 |
| Secondary | S.K 12/2 | 320 | 1280$^W$ | 2560$^W$ | 1280 | 2560 | 20 | 1280 | 128 | 640 ↑ | 6.5 | 30.1 |
|  | Y.N 11/5 | 2560 | 1280 | 640 | 1280 | 2560 | 20 | 1280 | 128 | 1280 | 15.1 | 12.9 |
|  | S.N 7/22 | 2560$^W$ | 1280 | 1280 | 1280 | 2560 | 5 | 1280 | 128 | 1280 | 13.3 | 16.6 |
| Late Latent | H.Y 2/1 | (—) | (—) | 160 | 320 | 160 | (—) | 320 | 1 | 5 | 0 | 2.5 |
|  | A.Y 4/3 | (—) | (—) | 160 | 320 | 160 | (±) | 80 | 4 | 10 | 0 | 2.3 |
|  | T.K 5/20 | (—) | (—) | 640$^W$ | 320 | 160 | (—) | 20 | (ND) | 80 | 0 | 4.7 |

( (—) Nonreactive  640 ↑ Greater than 640 times
  (±) Borderline  (ND) Not Determined
   W  weak )

( γ: IgG, γ-chains specific
  μ: IgM, μ-chains specific )

As can be seen from the table, the results of the present method (HIA) are substantially identical with the gel filtration method which is the most reliable method to determine IgM and IgM.

EXAMPLE 2

Using AM-RBC and TP-RBC, IgM of the serum of a primary syphilis and of the serum of a late latent syphilis were measured by the HIA method.

The washing process using the saline solution after the reaction with the anti immunoglobulin antibody sensitized on carrier particles was conducted once or twice, and the measuring procedures were the same as in paragraph (iv) supra of Example 1.

The results are shown in the following table.

| Serum | Washing Time | Antibody Titer |
|---|---|---|
| Primary Syphilis | 1 | 1:1280 |
|  | 2 | 1:1280 |
| Late Latent Syphilis | 1 | (—) |
|  | 2 | (—) |

As seen from the data, the antibody titer was not lowered by the washing.

EXAMPLE 3

IgM of the same serum as employed in Example 2 was measured by the HIA method where the order of the reaction with the anti immunoglobulin antibody sensitized on carrier particles and the reaction with the antigen sensitized on carrier particles was changed. Thus, the sample serum was first reacted with TP-RBC and the TP-RBC was washed with a saline solution and then AM-RBC was added to the washed TP-RBC.

Other than the above, the measuring procedures were the same as in paragraph (iv) supra of Example 2.

The results are shown in the following table.

| Serum | Washing Time | Antibody Titer |
|---|---|---|
| Primary Syphilis | 1 | 1:1280 |
|  | 2 | 1:1280 |
| Late Latent Syphilis | 1 | 1:160 |
|  | 2 | 1:40 (—) |
|  | 3 | 1:20 (—) |

In this method, more than two washings are necessary to avoid false positive by IgG of the TP.

We claim:

1. A method of measuring anti TP IgM antibodies in a sample comprising the steps of:
    (1) adding animal erythrocytes having anti IgM antibodies immobilized thereon, to a liquid sample containing IgM antibodies which have been produced by TP antigens, to allow said anti IgM antibodies to react with said IgM antibodies;
    (2) separating from the liquid the animal erythrocytes having anti IgM antibodies immobilized thereon, and which have reacted with said IgM antibodies in step (1);
    (3) adding animal erythrocytes having TP antigens immobilized thereon, to a liquid containing said animal erythrocytes separated in step (2) to react TP antigens with IgM antibodies which are specifically reactive to TP antigens, said IgM antibodies being anti TP IgM antibodies, and
    (4) correlating the agglutination due to the reaction in step (3) with the amount of anti TP IgM antibodies in the sample.

2. The method of claim 1 wherein said animal erythrocytes are selected from the group consisting of sheep erythrocytes and chicken erythrocytes.

3. The method of claim 1 wherein said separation is carried out by centrifuging.

4. The method of claim 1 wherein said animal erythrocytes separated in step (2) are washed, and then contacted with a syphilis antigen immobilized on animal erythrocytes.

* * * * *